(12) United States Patent
Cima et al.

(10) Patent No.: US 7,008,634 B2
(45) Date of Patent: *Mar. 7, 2006

(54) CELL GROWTH SUBSTRATES WITH TETHERED CELL GROWTH EFFECTOR MOLECULES

(75) Inventors: Linda G. Cima, Lexington, MA (US); Edward W. Merrill, Belmont, MA (US); Philip R. Kuhl, Arlington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 250 days.

This patent is subject to a terminal disclaimer.

(21) Appl. No.: 08/398,555

(22) Filed: Mar. 3, 1995

(65) Prior Publication Data

US 2004/0214997 A1    Oct. 28, 2004

(51) Int. Cl.
*A61K 38/18* (2006.01)
*A61K 47/30* (2006.01)
*C12Q 1/02* (2006.01)
*C12N 11/08* (2006.01)

(52) U.S. Cl. ............ 424/423; 424/426; 424/443; 424/484; 424/486; 424/488; 435/29; 435/178; 435/179; 435/180; 435/181; 435/182; 435/370; 435/372; 435/398; 435/399; 435/400; 435/402; 514/12; 514/21; 530/812; 530/815; 530/816

(58) Field of Classification Search ............ 424/484, 424/423, 426, 443, 447, 486, 487, 488, DIG. 16; 435/177, 178, 179, 180, 181, 240.2, 240.21, 435/240.24, 240.241, 240.25, 240.46, 288.1, 435/29, 240.23, 240.243, 370, 372, 398, 435/399, 400, 401, 402; 514/12, 21; 530/810–816, 530/408, 411, 409, 410

See application file for complete search history.

(56) References Cited

U.S. PATENT DOCUMENTS 4,060,081 A    11/1977    Yannas et al. ............ 602/49

(Continued)

FOREIGN PATENT DOCUMENTS

| EP | 0 531 733 A1 | 3/1993 |
| JP | 4108377 | 4/1992 |
| WO | WO 89/05616 | 6/1989 |
| WO | WO 91/01760 | 2/1991 |
| WO | WO 94/28937 | 12/1994 |

OTHER PUBLICATIONS

"Peptide Growth and Their Receptors I" M.B. Sporn and A.B. Roberts, eds. (Springer-Verlag, New York, 1990).

(Continued)

*Primary Examiner*—Jeffrey Edwin Russel
(74) *Attorney, Agent, or Firm*—Pabst Patent Group LLP

(57) ABSTRACT

Described are compositions with tethered growth effector molecules, and methods of using these compositions for growing cells and tissues. Growth effector molecules, including growth factors and extracellular matrix molecules, are flexibly tethered to a solid substrate. The compositions can be used either in vitro or in vivo to grow cells and tissues. By tethering the growth factors, they will not diffuse away from the desired location. By making the attachment flexible, the growth effector molecules can more naturally bind to cell surface receptors. A significant feature of these compositions and methods is that they enhance the biological response to the growth factors. The method also offers other advantages over the traditional methods, in which growth factors are delivered in soluble form: (1) the growth factor is localized to a desired target cell population; (2) significantly less growth factor is needed to exert a biologic response. This method can be used as a means of enhancing the therapeutic use of growth factors in vivo and of creating surfaces which will enhance in vitro growth of difficult-to-grow cells such as liver cells.

7 Claims, 1 Drawing Sheet

U.S. PATENT DOCUMENTS

| | | | | |
|---|---|---|---|---|
| 4,352,883 | A | | 10/1982 | Lim .......................... 435/178 |
| 4,458,678 | A | | 7/1984 | Yannas et al. ................ 612/48 |
| 4,485,097 | A | | 11/1984 | Bell .......................... 424/549 |
| 4,520,821 | A | | 6/1985 | Schmidt et al. ............. 606/151 |
| 4,954,637 | A | * | 9/1990 | Nitecki et al. .............. 548/546 |
| 5,032,508 | A | * | 7/1991 | Naughton et al. ............. 435/32 |
| 5,171,264 | A | | 12/1992 | Merrill .......................... 623/3 |
| 5,275,838 | A | | 1/1994 | Merrill ................... 351/160 R |
| 5,370,681 | A | * | 12/1994 | Herweck et al. ............... 623/1 |
| 5,414,075 | A | * | 5/1995 | Swan et al. ................. 568/333 |
| 5,508,164 | A | * | 4/1996 | Kausch et al. ................. 435/6 |
| 5,512,474 | A | * | 4/1996 | Clapper et al. ....... 435/240.243 |
| 5,522,895 | A | * | 6/1996 | Mikos .......................... 623/16 |
| 5,906,828 | A | * | 5/1999 | Cima et al. ................. 424/423 |
| 6,045,818 | A | * | 4/2000 | Cima et al. ................. 424/423 |

OTHER PUBLICATIONS

"Protein immobilization: fundamentals and applications" Richard F. Taylor, ed, (M. Dekker, New York, 1991).

Cima and Langer, "Engineering Human Tissue" *Chem. Eng. Prog.* 89: 46-54 (1993).

Cima, et al., "Hepatocyte Culture on Biodegradable Polymeric Substrates," *Biotechnology and Bioengineering* 38: 145-158 (1991).

Engleberg and Kohn, "Physico-mechanical properties of degradable polymers used in medical applications: a comparative study," *Biomaterials* 12: 292-304 (1991).

Freshney, *Cell Culture, a manual of basic technique*, Third Edition (Wiley-Liss, New York, 1994).

Galloway et al., "Development of a Standard Protocol for In Vitro Cytogenetic Testing With Chinese Hamster Ovary Cells," *Environ. Mutagen.* 7: 1 (1985).

Gnanou et al., "Synthesis of star-shaped poly(ethylene oxide)," *Makromol. Chemie* 189: 2885-2892 (1988).

Haworth et al., "Salmonella Mutagenicity Test Results for 250 Chemicals," *Environ. Mutagen.* 5 (suppl. 1): 3 (1983).

Jauregui et al., "Attachment and Long Term Survival of Adult Rat Hepatocytes in Primary Monlayer Cultures: Comparison of Different Substrata and Tissue Culture Media Formulations," *In Vitro Cellular & Developmental Biology* 22: 13-22 (1986).

Kleinman, et al., "Use of Extracellular Matrix Components for Cell Culture," *Analytical Biochemistry* 166: 1-13 (1987).

Merrill, "Poly(ethylene oxide) star molecules: Synthesis, characterization, and applications in medicine and biology," *J. Biomater. Sci. Polymer Edn* 5: 1-11 (1993).

Mooney, et al., "Switching from Differentiation to Growth in Hepatocyctes: control by Extracellular Matrix," *Journal of Cellular Physiology* 151: 497-505 (1992).

Mortelmans, et al., "Mutagenicity Testing of Agent Orange Components and Related Chemicals," *Toxicol. Appl. Pharmacol.* 75: 137 (1984).

Myhr, et al., "Evalauation of Short-Term Tests for Carcinogens: Report of the International Programme on Chemical Safety's Collaborative Study on *in vitro* Assays", *Progress in Mutation Research Series*, vol. 5, pp. 55-568, Ashby et al., Editors (Elsevier, Amsterdam, 1985).

Reddy, et al., "Proliferative Response of Fibroblasts Expressing Internalization-Deficient Epidermal Growth Factor (EGF) Receptors Is Altered via Differential EGF Depletion Effect," *Biotechnology Progress* 10: 377-384 (1994).

Sontag et al., "Guidelines for Carcinogen Bioassay in Small Rodents," *U.S. Dep. Health Educ. Welfare Publ. (NIH) Carcinog. Tech. Rep. Serv.* 1: 76 (1976).

Tomomura, et al., "The Control of DNA Synthesis in Primary Cultures of Hepatocytes from Adult and Young Rats: Interactions of Extracellular Matrix Components, Epidermal Growth Factor, and the Cell Cycle," *J. of Cellular Physiology* 30:221-227 (1987).

Vacanti et al., "Beyond Transplantation," *Arch. Surg.* 123: 545-549 (1988).

\* cited by examiner

CELL GROWTH SUBSTRATES WITH TETHERED CELL GROWTH EFFECTOR MOLECULES

The government has certain rights in the invention since this invention was made with government support under Grant Number 9157321-BCS awarded by the National Science Foundation.

BACKGROUND OF THE INVENTION

This invention concerns cell and tissue growth substrates, growth stimulation compositions, and methods for delivering growth factors to cells and tissues.

Long-term mammalian cell culture has been difficult to achieve. Many types of specialized cells plated on standard tissue culture plastic dishes dedifferentiate, lose function, and fail to proliferate. There are many applications of mammalian cell culture that could benefit from methods or materials which enhance the long term stability of differentiated mammalian cells in culture. These cells are currently used as sources of natural and engineered proteins and glycoproteins, in screens for the effects of compounds on cell proliferation and function, and for implantation to supplement or replace cell function. Certain cells are particularly difficult to maintain in long term culture, such as hepatocytes.

It would be especially useful if hepatocytes could be maintained in long term culture. For example, in vitro toxicity testing of ingestibility orally administered compounds has been hampered by the fact that the liver converts many compounds into other chemical forms. These other forms may be toxic or have other effects. Thus complete testing of materials in cell culture must include the effects of biotransformations carried out by the liver. Using current methodology, it is difficult to grow normal liver cells in vitro beyond two to three cell divisions. The result is that in vitro testing does not reduce the number of animals needed because essentially all of the cells to be used in vitro must come from direct isolation. A method of expanding liver cells in vitro would make it feasible to use in vitro liver cell cultures to carry out biotransformations by applying the compound of interest directly to liver cells in culture. The supernate from the liver cell cultures could then be applied to other types of cells, such as skin, lung, nerve, and bladder, to assess the effect of the metabolized compound of interest.

Studies have been conducted for a number of years to improve the viability, proliferation and differentiated function of eukaryotic cells cultured in vitro. One discovery has been the importance of the extracellular matrix and extracellular matrix molecules in maintaining cell function and allowing cell growth. These effects and methods of using matrix components for cell growth, have been described by, for example. Jauregui et al., *In Vitro Cellular & Developmental Biology* 22: 13–22 (1986), Kleinman et al., *Analytical Biochemistry* 166: 1–13 (1987), and Mooney et al., *Journal of Cellular Physiology* 151: 497–505 (1992).

Growth factors, such as epidermal growth factor (EGF), platelet-derived growth factor (PDGF), and transforming growth factors (TGFα, TGFβ), exert a broad mitogenic response. Growth factors and their effects have been described in "Peptide Growth Factors and Their Receptors I" M. B. Sporn and A. B. Roberts, eds. (Springer-Verlag, New York, 1990). In recognition of their importance, most cell and tissue growth compositions include growth factors, either as an additive or as a component of complex growth media. The use of growth factors in this manner has certain drawbacks. For example, cells have a complex, nonlinear response to the concentration of growth factor in their environment. Extended exposure to high growth factor concentrations may cause cells to lose responsiveness to the factor. For example, EGF, a potent mitogen for a wide variety of cell types and arguably the best-characterized of the growth factors, when delivered in soluble form, is typically internalized by the cell, and the cell often responds by a down-regulating the number of EGF receptors. This down-regulation causes cells to lose responsiveness to EGF.

Growth factors have also been used in disappointingly few clinical products, considering the range of effects they produce in vitro. Translation of the mitogenic effects observed for the target cell in vitro to tissue growth in vivo is hampered by several issues. For example, the growth factors, when placed in a complex cellular environment, often end up stimulating the growth of competing cells which then overgrow the target cells. Researchers have attempted to solve this problem by targeting delivery of factors at a specific site, but this approach is not always successful because soluble growth factors can readily diffuse into the blood stream and away from the target site, exerting their effects elsewhere. This diffusion of growth factors is also a problem because it increases the amount of growth factor that must be used in order to have the desired local effect. Internalization of growth factors and loss of responsiveness to growth factors is a particular problem for in vivo applications considering the amount of time cell growth must be stimulated to allow wound healing.

Another attempt to improve the longevity of growth factor effects in vivo has been to incorporate growth factors in a slow release material. Such a scheme still requires large amounts of growth factor and does not address the problem of competing cell growth due to diffusion of the growth factors. The large amount of growth factors needed for these cell and tissue growth methods is a particular problem because growth factors are difficult and expensive to prepare.

It is therefore an object of the invention to provide a cell and tissue growth substrate that stimulates long-term target cell growth.

It is another object of the invention to provide a tissue growth scaffold for growth of a target tissue in vivo.

It is a further object of the invention to provide a method of long-term cell and tissue growth in vitro, and to provide a method of growing target tissue in vivo.

It is another object of the invention to provide an in vitro tissue analog for drug and toxicity testing, and a method of drug and toxicity, testing using the tissue analog.

SUMMARY OF THE INVENTION

The methods and compositions described herein concern new cell and tissue growth substrates. Growth effector molecules, including growth factors and extracellular matrix molecules, are flexibly tethered to a support medium and the combination is used to stimulate and support cell and tissue growth. The most significant feature of these compositions is that they enhance the biological response to the growth factor. The new compositions also offer other advantages over the traditional growth methods, in which growth factors are delivered in soluble form: (1) the growth factor is localized to a desired target cell population, and (2) significantly less growth factor is needed to exert a biologic response. In a preferred embodiment, multiple growth factors and/or matrix materials are attached to a single core molecule, such as a star polymer. These compositions can be used as a means of enhancing the therapeutic use of growth factors in vivo and of creating surfaces which will enhance in vitro growth of difficult-to-grow cells such as liver cells.

DETAILED DESCRIPTION OF THE INVENTION

Figure 1:
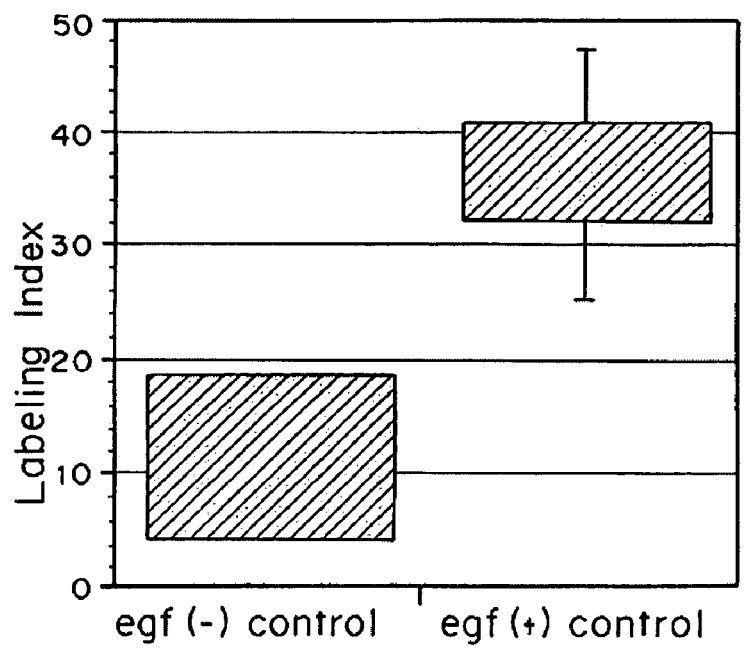
FIG. 1 is a graph of DNA synthesis in cells grown on a non-tethered substrate, with EGF present or absent from the growth medium, plotting labeling index versus the presence or absence of EGF. The labeling index is the percentage of cells in a field that have stained nuclei.

Many problems with effective utilization of growth factors may be overcome if, instead of being delivered in soluble form, the growth factors are immobilized on a solid substrate. This approach is attractive because some forms of insoluble matrix, such as crosslinked collagen sponges and bioresorbable polyester fabric, are used for many types of tissue regeneration to provide a template for tissue growth. The solid support need not be permanent, and thus the approach may be used for almost any tissue. Immobilization prevents the factor from diffusing away from the site and consequently allows a much more highly targeted form of delivery than other methods. Besides this concentration effect, tethering has other powerful advantages, stemming from the way growth factors work. For example, when delivered in soluble form, EGF is typically internalized by the cell, and the cell often responds by down-regulating the number of EGF receptors. However, evidence now shows that the growth factor does not have to be internalized in order to stimulate cell growth. For example, Reddy et al., *Biotechnology Progress* 10: 377–384 (1994), describes fibroblasts that remain responsive to EGF despite their expression of internalization-deficient EGF receptors. As demonstrated by the following example, by allowing the target cell to bind EGF, but preventing the cell from internalizing the bound EGF, it is possible to circumvent the normal down-regulation of receptors that occurs in the presence of high concentrations of EGF. This offers two advantages: (1) it is possible to speed the rate of target cell growth in vivo because cells in contact with the surface bearing the growth factor do not lose their responsiveness to EGF, and (2) considerably less growth factor is required, because cells do not internalize and degrade the growth factor. The method of attachment of the growth factor to the substrate is critical because the receptor must have access to the factor. Furthermore, for some growth factors, dimerization or aggregation in the membrane is believed to be critical, as described in "Peptide Growth Factors and Their Receptors I" M. B. Sporn and A. B. Roberts, eds. (Springer-Verlag. New York. 1990). Thus, the growth factor will either have to be immobilized in extremely high concentration or immobilized on flexible tethers which will allow the ligand-receptor complex to aggregate in the cell membrane. Direct immobilization of even high concentrations of growth factor may be ineffective if the receptors bind randomly.

Tethers

Requirements

As used herein, a tether is a flexible link between an attachment substrate and a growth effector molecule. Flexible tethers for attaching growth effector molecules to a substrate must satisfy two important requirements: (1) the need for mobility of the ligand-receptor complex within the cell membrane in order for the effector molecule to exert an effect, and (2) biocompatibility of materials used for immobilization. Substantial mobility of a tethered growth factor is critical because even though the cell does not need to internalize the complex formed between the receptor and the growth factor, it is believed that several complexes must cluster together on the surface of the cell in order for the growth factor to stimulate cell growth. In order to allow this clustering to occur, the growth factors are attached to the solid surface, for example, via lone water-soluble polymer chains, which are referred to as tethers, allowing movement of the receptor-ligand complex in the cell membrane.

Examples of water-soluble, biocompatible polymers which can serve as tethers include polymers such as synthetic polymers like polyethylene oxide (PEO), polyvinyl alcohol, polyhydroxyethyl methacrylate, polyacrylamide, and natural polymers such as hyaluronic acid, chondroitin sulfate, carboxymethylcellulose, and starch.

Tethers can also be branched to allow attachment of multiple growth effector molecules in close proximity. Branched tethers can be used, for example, to increase the density of growth effector molecule on the substrate. Such tethers are also useful in bringing multiple or different growth effector molecules into close proximity on the cell surface. This is useful when using a combination of different growth effector molecules. Preferred forms of branched tethers are star PEO and comb PEO.

Star PEO is formed of many PEO "arms" emanating from a common core. Star PEO has been synthesized, for example, by living anionic polymerization using divinylbenzene (DVB) cores, as described by Gnanou et al., *Makromol. Chemie* 189: 2885–2892 (1988), and Merrill, *J. Biomater. Sci. Polymer Edn* 5: 1–11 (1993). The resulting molecules have 10 to 200 arms, each with a molecular weight of 3,000 to 12,000. These molecules are about 97% PEO and 3% DVB by weight. Other core materials and methods may be used to synthesize star PEO. Comb PEO is formed of many PEO chains attached to and extending from the backbone of another polymer, such as polyvinyl alcohol. Star and comb polymers have the useful feature of grouping together many chains of PEO in close proximity to each other.

Length

The length of a tether is limited only by the mechanical strength of the tether used and the desired stability of a tethered growth factor. It is expected that stronger tethers can be made longer than weaker tethers, for example. It is also desirable for tether length and strength to be matched to give a desired half life to the tether, prior to breakage, and thereby adjust the half life of growth factor action. The minimum tether length also depends on the nature of the tether. A more flexible tether will function well even if the tether length is relatively short, while a stiffer tether may need to be longer to allow effective contact between a cell and the growth effector molecules.

The backbone length of a tether refers to the number of atoms in a continuous covalent chain from the attachment point on the substrate to the attachment point of the growth effector molecule. All of the tethers attached to a given substrate need not have the same backbone length. In fact, using tethers with different backbone lengths on the same substrate can make the resulting composition more effective and more versatile. In the case of branched tethers, there can be multiple backbone lengths depending on where and how many growth effector molecules are attached. Preferably, tethers can have any backbone length between 5 and 50,000 atoms. Within this preferred range, it is contemplated that backbone length ranges with different lower limits, such as 10, 15, 25, 30, 50, and 100, will have useful characteristics.

Such tethers are not intended to be limited by the manner in which the substrate-tether-growth effector molecule composition is assembled. For example, if linker molecules are attached to the substrate and the growth effector molecule, and then the linkers are joined to form the tethered composition, the entire length of the joined linkers is considered the tether. As another example, the attachment substrate may, by its nature, have on its surface protruding molecular chains. If a linker molecule is attached to the substrate via such protruding chains, then the chain and linker together are considered to be a tether.

Biocompatible polymers and spacer molecules are well known in the art and most are expected to be suitable for forming tethers. The only important characteristics are biocompatibility and flexibility. That is, the tether should not be made of a substance that is cytotoxic or, in the case of in vivo uses, which causes significant allergic or other physiological reaction when implanted. The tether should also allow the growth factor a sufficient range of motion to effectively bind to a cell surface receptor.

The biodegradability of a tether, the tether-substrate link, or the tether-growth factor link can be used to regulate the length of time a growth factor stimulates growth. For example, if a given tether degrades during cell growth at a consistent rate, then a limit can be placed on how long the growth factors binds to and stimulates cell growth. Once untethered, a growth factor can be internalized by the cell or can diffuse away from the target cells. Such planned degradation is especially useful in the context of implanted compositions, used to stimulate tissue replacement, by limiting the amount of tissue growth.

Attachment Substrates

There are two basic types of substrates onto which growth effector molecules can be tethered. One class includes biocompatible materials which are not biodegradable, such as polystyrenes, polyethylene vinyl acetates, polypropylenes, polymethacrylates, polyacrylates, polyethylenes, polyethylene oxides, glass, polysilicates, polycarbonates, polytetrafluoroethylene, fluorocarbons, nylon, silicon rubber, and stainless steel alloys. The other class of materials includes biocompatible, biodegradable materials such as polyanhydrides, polyglycolic acid, polyhydroxy acids such as polylactic acid, polyglycolic acid, and polylactic acid-glycolic acid copolymers, polyorthoesters, polyhydroxybutyrate, polyphosphazenes, polypropylfumerate, and biodegradable polyurethanes, proteins such as collagen and polyamino acids, and polysaccharides such as glycosaminoglycans, alginate, and carageenan, bone powder or hydroxyapatite, and combinations thereof. These biodegradable polymers are preferred for in vivo tissue growth scaffolds. Other degradable polymers are described by Engleberg and Kohn, *Biomaterials* 12: 292–304 (1991).

Attachment substrates can have any useful form including bottles, dishes, fibers, woven fibers, shaped polymers, particles and microparticles. For in vitro cell growth, the growth effector molecule can be tethered to standard tissue culture polystyrene petri dishes. Woven fibers are useful for stimulating growth of tissue in the form of a sheet, sponge or membrane.

The biodegradability of a substrate can be used to regulate the length of time the growth factor stimulates growth and to allow replacement of implanted substrate with new tissue. For this purpose the substrate with tethered growth effector molecules can be considered a scaffold upon which new tissue can form. As such, a degradable scaffold is broken down as tissue replacement proceeds. Once released from the substrate, a growth factor can be internalized or can diffuse away from the target cells. Such planned degradation is especially useful in the context of implanted compositions, used to stimulate tissue replacement, by limiting the amount of tissue growth and eliminating the need to remove the tissue scaffold. For implantation in the body, preferred degradation times are typically less than one year, more typically in the range of weeks to months.

In some embodiments, attachment of the cells to the substrate is enhanced by coating the substrate with compounds such as extracellular membrane components, basement membrane components, agar, agarose, gelatin, gum arabic, collagen types I, II, III, IV, and V, fibronectin, laminin, glycosaminoglycans, mixtures thereof, and other materials known to those skilled in the art of cell culture.

Growth Effector Molecules

Growth effector molecules, as used herein, refer to molecules that bind to cell surface receptors and regulate the growth, replication or differentiation of target cells or tissue. Preferred growth effector molecules are growth factors and extracellular matrix molecules. Examples of growth factors include epidermal growth factor (EGF), platelet-derived growth factor (PDGF), transforming growth factors (TGFα, TGFβ), hepatocyte growth factor, heparin binding factor, insulin-like growth factor I or II, fibroblast growth factor, erythropoietin, nerve growth factor, bone morphogenic proteins, muscle morphogenic proteins, and other factors known to those of skill in the art. Additional growth factors are described in "Peptide Growth Factors and Their Receptors I" M. B. Sporn and A. B. Roberts, eds. (Springer-Verlag, New York, 1990), for example.

Growth factors can be isolated from tissue using methods known to those of skill in the art. For example, growth factors can be isolated from tissue, produced by recombinant means in bacteria, yeast or mammalian cells. For example, EGF can be isolated from the submaxillary glands of mice and Genentech produces TGF-β recombinantly. Many growth factors are also available commercially from vendors, such as Sigma Chemical Co, of St. Louis, Mo., Collaborative Research, Genzyme, Boehringer, R&D Systems, and GIBCO, in both natural and recombinant forms.

Examples of extracellular matrix molecules include fibronectin, laminin, collagens, and proteoglycans. Other extracellular matrix molecules are described in Kleinman et al. (1987) or are known to those skilled in the art. Other growth effector molecules useful for tethering include cytokines, such as the interleukins and GM-colony stimulating factor, and hormones, such as insulin. These are also described in the literature and are commercially available.

The specific function or effect of a growth effector molecule does not limit its usefulness in the disclosed compositions and methods. This is because tethering of a growth effector molecule is used to prevent loss of effect caused by diffusion away from a target cell and/or internalization of a growth factor.

Only those growth effector molecules that can exert an effect while tethered are useful in the disclosed compositions. Such an effect, however, need not be the same effect or require the same concentration as the untethered growth effector molecule. So long as a growth effector molecule can exert any desired growth effect on a cell while tethered it is considered to be useful for tethering. These useful effects can be determined by tethering a selected growth effector molecule and observing the effect on cell growth using growth assays, such as those described in the examples below.

Attachment Methods

Standard immobilization chemistries, which are well known in the art, can be used to covalently link the tethers to the growth effector molecule and the substrate. Tethering growth effector molecules can be accomplished by attachment, for example, to aminated surfaces, carboxylated surfaces or hydroxylated surfaces using standard immobilization chemistries. Examples of attachment agents are cyanogen bromide, succinimide, aldehydes, tosyl chloride, avidin-biotin, photocrosslinkable agents, epoxides and maleimides. A preferred attachment agent is glutaraldehyde. These and other attachment agents, as well as methods for their use in attachment, are described in "Protein immobilization: fundamentals and applications" Richard F. Taylor, ed. (M. Dekker, New York. 1991). Growth effector molecules can be tethered to a substrate by chemically cross-linking a tether molecule to reactive side groups present within the substrate and to a free amino group on the growth effector molecule. For example, synthetic EGF may be chemically cross-linked to a substrate that contains free amino or carboxyl groups using glutaraldehyde or carbodiimides as cross-linker agents. In this method, aqueous solutions containing free tethers molecules are incubated with the substrate in the presence of glutaraldehyde or carbodiimide. For crosslinking with glutaraldehyde the reactants can be incubated with 2% glutaraldehyde by volume in a buffered solution such as 0.1 M sodium cacodylate at pH 7.4. Other standard immobilization chemistries are known by those of skill in the art and can be used to join substrates, tethers, and growth effector molecules.

For the disclosed cell growth compositions, growth effector molecules may be tethered either alone or in combinations. For example, both insulin and EGF may be tethered to the same substrate. The growth effector molecules may be combined in any desired proportions. The relative amounts of different growth effector molecules can be controlled, for example, by first separately linking the growth effector molecules to tethers, then mixing the "loaded" tethers in the desired proportions and attaching them to the substrate. The proportion of each growth effector molecule tethered to the substrate should match the proportion of loaded tethers in the attachment reaction.

Tethering to Aminated Surfaces.

Cell culture surfaces bearing primary amines can be prepared, for example, by amino-siloxane treatment of glass using reagents which can be commercially purchased and applied to standard laboratory glassware or by plasma discharge treatment of polymers in an ammonia environment. Collagen matrices for tissue regeneration have primary amines present in lysine side chains and the terminal amines of each molecule. Two approaches are possible. Polymers such as PEO tethers can be activated on both ends with a leaving group such as tresyl chloride which reacts with primary amines. No blocking is necessary because only the terminal hydroxyl residues of tethers are reactive. This type of reaction can be carried out using standard glassware in a chemical fume hood. Vacuum drying of the product is required as an intermediate step. A substantial excess of the activated tether over the number of available amines, dissolved in a saline buffer, is added to the surface to be modified and the coupling reaction is allowed to proceed. Use of an excess of activated PEO in this step minimizes the reaction of both ends of PEO with available amines and ensures that a substantial fraction of unreacted activated chain ends are left for reaction with the growth factor. Unreacted PEO is washed away, and the EGF is then added in saline solution to react with the remaining activated chain ends. If mouse EGF is used, only the terminal amino acid is reactive because it contains no other primary amines. Human EGF contains three possible immobilization sites. After the reaction is completed, excess unreacted growth factor is removed. This first approach is preferred for attaching EGF to a matrix such as crosslinked collagen, which contains a large number of free hydroxyls and which does not allow significant non-specific adsorption of EGF.

A second approach is to activate the tethers on only one end initially by using a substoichiometric amount of activating agent. This will yield a distribution of species which include completely unactivated tether as well as tether activated at both ends. Unactivated tether can easily be washed away after the attachment step. The tether is then coupled to the support as described above, and the free tether ends are then activated to allow attachment of EGF. This second approach is preferred for derivatization of cell culture surfaces, which might allow substantial non-specific adsorption of growth factor, because an intermediate step in which unreacted amines are blocked with short-chain monomethoxy PEO can be added before EGF attachment in order to minimize non-specific adsorption of the factor.

Cells

Cells to be cultured using the disclosed compositions can be any cells that respond to growth factors or that need growth effector molecule for growth. For example, cells can be obtained from established cell lines or separated from isolated tissue. Cells types that can be used with the tethered growth effector molecule compositions include most epithelial and endothelial cell types, for example, parenchymal cells such as hepatocytes, pancreatic islet cells, fibroblasts, chondrocytes, osteoblasts, exocrine cells, cells of intestinal origin, bile duct cells, parathyroid cells, thyroid cells, cells of the adrenal-hypothalamic-pituitary axis, heart muscle cells, kidney epithelial cells, kidney tubular cells, kidney basement membrane cells, nerve cells, blood vessel cells, cells forming bone and cartilage, and smooth and skeletal muscle. The cells used can also be recombinant. Methods for gene transfer are well known to those skilled in the art.

In Vitro Cell and Tissue Growth Using Substrates with Tethered Growth Effector Molecules Substrates with tethered growth effector molecules can be used to improve in vitro culture of hard-to-grow cells such as liver cells. Liver cell cultures would be useful for toxicology testing to replace certain aspects of animal testing of drugs. Liver cells grow very poorly in vitro using prior art methods, typically undergoing only one or two rounds of DNA synthesis after they are placed in culture. Since a tethered growth factor cannot be internalized, tethering will change the way the cells respond to the factor, constantly stimulating them to grow.

Cells can be cultured with tethered growth effector molecule compositions using any of the numerous well known cell culture techniques. Standard cell culture techniques are described in Freshney, "Cell Culture, a manual of basic technique" Third Edition (Wiley-Liss, New York, 1994). Other cell culture media and techniques well known to those skilled in the art can be used with the disclosed compositions. The disclosed compositions are adaptable to known cell culture vessels. For example, growth effector molecules can be immobilized on standard tissue culture polystyrene and glass petri dishes, T-flasks, roller bottles, stackable chambers, and filter systems such as the Millipore MILLI-CELL™ inserts, hollow fiber reactors and microcarriers. Cells can also be cultured in suspension using the disclosed compositons by tethering growth effector molecules to tiny beads or fibers, on the order of 10 microns in diameter of length. Such tiny particles, when added to culture medium, would attach to cells thereby stimulating their growth and providing attachment signals. The only critical difference in culturing technique is the elimination of growth factor from the cell culture medium when using tethered growth factor compositions. As described in the examples below, using soluble versus tethered EGF in primary hepatocyte cultures show an enhanced DNA synthesis rate of the tethered growth factor in comparison to the soluble growth factor. This effect is dependent on the amount of the immobilized factor.

In Vivo Tissue Growth Using Tissue Growth Scaffolds with Tethered Growth Effector Molecules In yet another embodiment of the present invention, erodible and non-erodible artificial matrices with tethered growth effector molecules may be used either alone or in combination with attached cells to remodel tissue architecture or to repair tissue defects and wounds.

Known methods and compositions for culturing cells and implanting them into the body can be adapted to use tethered growth effector molecules. For example, U.S. Pat. No. 4,352,883 to Lim, uses cells that are encapsulated within alginate microspheres, then implanted. Such microspheres can be modified with tethered growth effector molecules to improve their usefulness. Culturing cells on a matrix for use as artificial skin, as described by Yannas and Bell in a series of publications, can also be modified by tethering growth effector molecules to the matrix. U.S. Pat. No. 4,485,097 to Bell, U.S. Pat. No. 4,060,081 to Yannas et al., and U.S. Pat. No. 4,458,678 to Yannas et al. describe substrates for use as artificial skin. U.S. Pat. No. 4,520,821 to Schmidt describes a similar approach that was used to make linings to repair defects in the urinary tract.

Vacanti et al., *Arch. Surg.* 123: 545–549 (1988), describes a method of culturing dissociated cells on biocompatible, biodegradable matrices for subsequent implantation into the body. Cima and Langer, "Tissue Engineering" *Chem. Eng. Prog.* 89: 46–54 (1993), describe important considerations for the nature and form of implanted matrices useful for inducing tissue replacement. U.S. patent application Ser. No. 08/200,636 entitled "Tissue Regeneration Matrices by Solid Free Force Fabrication" filed Feb. 23, 1994 by Cima and Cima, which is hereby incorporated by reference, describes tissue regeneration matrices, fabrication techniques, and methods of regenerating tissue. In general, tissue regeneration devices can be constructed from polymers, ceramics, or from composites of ceramics and polymers. Common materials useful for constructing tissue regeneration devices are, for example, extracellular matrix proteins, especially collagens; degradable polyesters, such as polylactic acid, polyglycolic acid, co-polymers of polylactic acid and polyglycolic acid, and polycapralactone; polyhydroxybutyrate; polyanhydrides; polyphosphazenes; bone powder; natural polysaccharides, such as hyaluronic acid, starch, and alginate; hydroxyapatite; polyurethanes; and other degradable polymers described by Engleberg and Kohn, *Biomaterials* 12: 292–304 (1991). All of these known compositions can be modified by tethering growth effector molecules to the substrate.

Growth effector molecule tethered compositions for in vivo use can be in the form of polymeric, attachment molecule-coated sutures, pins, wound dressings, fabric, and space-filling materials. Attachment substrates that promote ingrowth of dermal fibroblasts and capillaries could also be used for dermatological applications and cosmetic surgery, such as repair of wrinkles and aging skin, burn therapy, or skin reconstruction following disfiguring surgery. Substrates with tethered growth effector molecules that promote osteoblast migration could be used to fill bone defects following tumor surgery or for non-healing fractures. Substrates with tethered growth effector molecules that promote muscle cell growth and migration could be used for replacement of muscle mass, including cardiac muscle and smooth muscle, following disfiguring surgery and for patients with muscle degeneration or dysfunction. Tubular substrates with tethered growth effector molecules that promote growth, migration, and function of epithelial, endothelial and mesenchymal cells can be used for construction of artificial ducts for carrying bile, urine, gases, food, semen, cerebrospinal fluid, lymph, or blood. Sheaths formed of substrates that promote growth of fibroblasts from perichondrium, periosteum, dura mater, and nerve sheaths may be used to recreate these structures when they are injured or lost due to surgery or cancer. In all of these embodiments, either the substrate with tethered growth effector molecules or substrate plus attached cells may be used for reconstruction in vivo.

Substrates for promoting tissue generation can be formed to have a desired tissue shape. As used herein, a desired tissue shape is the shape that the newly generated tissue is desired to have. For example, certain tissues may need to be sheet-like, tubular, or formed as a lobe.

Deactivation of the growth factor once appropriate tissue regeneration has occurred can be accomplished by tethering the growth factor to a support which slowly degrades. Examples of such support materials are polylactide-co-glycolide and crosslinked hyaluronic acid or collagen. Properly shaped substrate with tethered growth effector molecules can be applied in clinical problems such as healing of skin or periodontal ligament by encouraging continued tissue growth for the life of a shaped, degradable implant.

The disclosed compositions can be administered to animals in various modes, including implantation, injection, and infusion. Known implantation techniques can be used for delivery of many different cell types to achieve different tissue structures. The tethered growth effector molecule compositions may be implanted in many different areas of the body to suit a particular application.

Drug and Toxicity Testing Using Tissue Grown In Vitro on Tethered Substrates

In another embodiment, cells are cultured on substrates with tethered growth effector molecules and the resulting cell cultures are used to screen compounds for effects on cell growth, cell proliferation, cell metabolism, and DNA. For example, the cultured cells can be used to screen for compounds that alter hepatocyte enzyme systems. The cultured cells can also be used to study metabolism of various compounds and the carcinogenicity or mutagenicity of compounds both before and after metabolism by the cells.

Classically, compounds have been assayed for mutagenic activity using short term tests (STT) employing bacterial cell systems or animal studies. Most animal studies are conducted using the protocol for rodents developed by the National Cancer Institute in the early 1970s and reported by Sontag et al. in *U.S. Dep. Health Educ. Welfare Publ.* (*NIH*) *Carcinog. Tech. Rep. Serv.* 1: 76 (1976). Four STTs that are routinely used are the *Salmonella* mutagenesis, SAL, described by Haworth et al., *Environ. Mutagen.* 5 (suppl. 1): 3 (1983) and Mortelmans et al. *Toxicol. Appl. Pharmacol.* 75: 137 (1984); chromosome aberrations in Chinese hamster ovary cells, ABS; sister chromatid exchanges in Chinese hamster ovary cells, SCE, both described by Galloway et al. *Environ. Mutagen.* 7: 1 (1985); and mouse lymphoma cell, MOLY, assays, described by Myhr et al., "Evaluation of Short-Term Tests for Carcinogens: Report of the International Programme on Chemical Safety's Collaborative Study on in vitro Assays" vol. 5 of *Progress in Mutation Research Series*, pages 55–568, Ashby et al., Editors (Elsevier, Amsterdam, 1985). Unfortunately, the correlation between the rodent assays and the STTs is poor, and the available STTs do not provide a method for testing compounds for toxicity or mutagenicity of normal organ-specific cells, nor the effect of metabolism on the compounds by the organ-specific cells, such as hepatocytes.

When testing the effect of potential toxins, control assays using known toxins are used for comparison. Examples of known hepatotoxins, such as acetaminophen, carbon tetrachloride, alcohol, and cell-specific viruses such as hepatitis viruses, can be used to test the suitability of the model tissue. Standard cell number or cell lysis assays, such as Lactate dehydrogenase release, can be used to measure toxicity. Numerous other toxicity and mutagenesis assays are known in the art and can be practiced using cell cultures grown on the tethered growth effector molecule substrates described herein.

The disclosed compositions can be used to grow liver cells in vitro and make it feasible to use in vitro liver cell cultures to carry out biotransformations by applying the compound of interest directly to liver cells in culture. The supernate from the liver cell cultures can then be applied to other types of cells, such as skin, lung, nerve, and bladder, to assess any derived effect of the compound of interest. An automated system which pumps culture medium through a liver cell culture and then to cultures of these other cell types can be used.

The present invention is further understood by reference to the following non-limiting Examples.

EXAMPLE 1

Enhancement of Cell Growth

Cell Growth and Cell Growth Assessment Methods

A. In Vitro Hepatocyte Culture System.

Rat hepatocytes were prepared according to Cima et al., *Biotechnology and Bioengineering* 38: 145–158 (1991). Briefly, rat livers were perfused with calcium-free perfusion buffer followed by perfusion buffer with $CaCl_2$ and collagenase until the livers became soft. Cells were dispersed in William's Medium E supplemented with 10 ng/mL EGF (Collaborative Research), 20 mM pyruvate (Gibco), 5 nM dexamethasone (Sigma), 20 mU/mL insulin (Gibco), 100 U/mL Penicillin/Streptomycin (Gibco). Cells were grown in culture generally as described by Cima et al. (1991). Briefly, cells were plated in culture medium at a concentration of $3 \times 10^4$ viable cells per square centimeter of culture surface area. Following attachment, the medium was changed to remove unattached cells and then cells were maintained in medium with daily medium changes. The base culture medium for growth on tethered substrates and control substrates was William's Medium E supplemented with 0.55 g/L sodium pyruvate. 0.5 pM dexamethasone. 0.8 mg/mL insulin (bovine). 100 U/mL Penicillin/Streptomycin, and 2 mM L-glutamine. In some cases, the medium was supplemented with EGF.

B. Quantitative Dot-Blot Assay.

Secretion rates for the proteins albumin, transferrin, fibrinogen, and fibronectin from the hepatocyte cultures were measured with a quantitative dot-blot assay. Media samples from the cultures were serially diluted and loaded in duplicate onto nitrocellulose paper with 0.1 micron pore size using a 96 well minifold apparatus (Schleicher-Schuell). Protein standards were also loaded in duplicate at decreasing levels from 300 to 10 ng/dot. The blot was then exposed to an appropriate primary antibody for the protein being quantitated. Rabbit anti-rat albumin and anti-rat transferrin were available from Cappel. Rabbit anti-rat fibrinogen was available from Sigma. The non-bound primary antibody was washed away after one hour, and the blot was exposed to donkey anti-rabbit IgG labelled with $^{125}I$ (Amersham) for an additional hour. The non-bound secondary antibody was washed away, and an autoradiograph of the blot was made. The dots were then punched out and bound $^{125}I$ measured using a gamma counter to determine the total amount of bound antibody. A calibration curve was generated by relating known amounts of standard protein to total count per minute bound. The linear portion of the standard curve was then used to quantitate the amount of protein in the unknown media samples. Secretion rates were normalized for cell number before the modulating effects of different attachment molecule densities were compared.

C. One Dimensional SDS-PAGE of Secreted Proteins.

The pattern of protein secretion from cultured hepatocytes was determined by pulse labelling cultures from 46 to 48 hours post-attachment with $^{35}S$ labelled methionine (ICN) in methionine free William's E media (Gibco), with or without EGF. The media was collected after the two hour labelling, and equal amounts of protein were analyzed by sodium dodecyl sulfate-polyacrylamide gel electrophoresis (SDS-PAGE). Autoradiographs were prepared with XOMAT-XAR5 film.

D. DNA Synthesis Measurement.

DNA synthesis is used as a measure of potential for cellular proliferation. Hepatocytes were pulse labelled for 20 hours beginning at 48 hours post-cell attachment with bromedeoxyuridine (BrdU), and subsequently fixed as outlined above. Cells were processed for immunocytochemistry using a BrdU kit from Amersham. Briefly, nuclei were permeabilized with DNAse I during incubation with the primary antibody. Detection of the bound antibody was achieved using peroxidase conjugated antibody to mouse immunoglobulin, and polymerizing diaminodenzidine (DAB) in the presence of cobalt and nickel, giving black staining at sites of BrdU incorporation. Alternatively, hepatocytes are pulse labelled for 16 hours beginning at 48 hours post-cell attachment with $^3H$-thymidine, and subsequently fixed in 95% ethanol/5% acetic acid fixative for several hours. The dishes or slides were coated with Kodak NTB2 autoradiography emulsion, and allowed to expose for seven days. Autoradiographic grains were developed using Kodak D-19 developer. The percentage of cells actively synthesizing DNA was quantitated by choosing 8 random areas on each dish and counting those cells with labelled nuclei versus the total number of cells. A minimum of 35 cells was counted per dish.

Synthesis of Growth Substrate Using Polyethylene Oxide Tether

A. Silyation Reaction.

Glass microscope slides were cleaned by immersion in 1:1 methanol:HCl for at least 30 minutes. They were rinsed twice in water and immersed in 1:1 water:concentrated sulfuric acid for at least 30 minutes. After another rise in water, the slides were placed in boiling water for 15 to 30 minutes. In a glove box under a nitrogen atmosphere, the freshly cleaned slides were placed in a solution of freshly mixed acidic methanol (1.0 mM acetic acid in methanol), 5.0% $H_2$, and 1% ETDA (N-(2-aminoethyl)(3-aminopropyl) trimethoxysilane) for 15 minutes, and then rinsed three times in methanol. Following the final rinse the slides were baked on a 120° C. oven for 5 to 10 minutes. The slides were stored in a desiccator at room temperature while awaiting polymer grafting.

B. Activation of Polymer.

Star polyethylene oxide was dissolved in methylene chloride (10 wt %) and dried over molecular sieve at 4° C. 110 microliters dry triethylamine and 75 microliters tresyl chloride were added to the dry polymer solution for every gram of polymer. After 90 minutes the solvent was evaporated under vacuum and the polymer was redissolved in acidified methanol (0.06 M HCl in methanol) and allowed to precipitate at −20° C. To remove unreacted tresyl chloride, the polymer was re-precipitated six times, after which the solvent was evaporated and the dried activated polymer stored under nitrogen.

C. PEO Grafting and Re-Activation.

Slides were grafted with star polyethylene oxide by placing a droplet of 0.1 to 10 wt % tresyl chloride activated polymer in 0.1 M phosphate buffer (pH 7.4) on each slide and allowing the reaction to proceed for 12 hours. The slides were rinsed in phosphate buffer and then in water. Slides were dried in graded ethanol solutions of, sequentially, 25%, 50%. 75%, and 100% ethanol. Then the slides were rinsed in dry acetone and finally in dry methylene chloride before reactivation. To tresyl activate the grafted star PEO, slides were immersed for 1 hour in 0.06 M tresyl chloride. 0.07 M triethylamine in methylene chloride at room temperature under a dry nitrogen atmosphere. For mock activation controls, the tresyl chloride was omitted.

D. EGF Coupling and Desorption.

$^{125}$-EGF of murine origin was coupled to activated slides in 0.01 M phosphate buffer (pH 7.4) for 12 hours at room temperature. The same procedure was followed for control slides. Adsorbed EGF was desorbed by successive washes in 0.01 M phosphate buffer (pH 7.4) with 0.1 wt % bovine collagen. The amount of EGF associated with the slides was determined using a gamma counter. The amount of EGF coupled to activated slides was determined by subtracting the amount adsorbed to the control slides from that associated with the activated slides.

Growth of Cells on Tethered Substrate In Vitro

Freshly isolated rat hepatocytes were seeded on tethered EGF slides and control slides, prepared as described above. The seeded slides were incubated in William's Medium E supplemented with 0.55 g/L sodium pyruvate, 0.5 pM dexamethasone, 0.8 mg/mL insulin (bovine), 100 U/mL Penicillin/Streptomycin, and 2 mM L-glutamine. Cells were labelled with bromedeoxyuridine (BrdU) as described above.

Cell seeding and DNA synthesis assays were performed on slides that had been activated with tresyl chloride and coupled with EGF, on mock activated control slides, both prepared as described above, and on control tissue-culture treated polystyrene dishes (Falcon) either with EGF added to the medium at 10 ng/mL or with EGF omitted.

Figure 2:
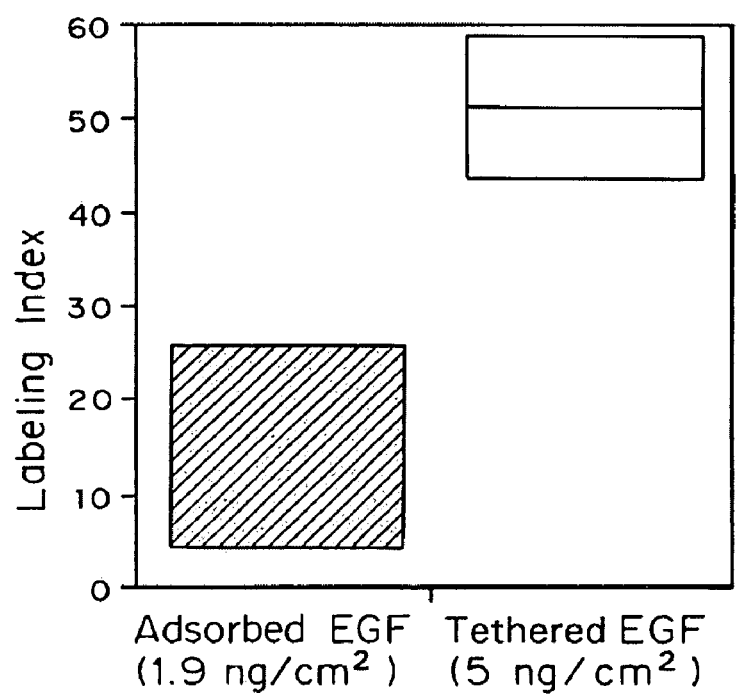
FIG. 2 is a graph of DNA synthesis in cells grown with tethered (coupled) or adsorbed EGF, plotting labeling index versus tethered or adsorbed EGF. The labeling index is the percentage of cells in a field that have stained nuclei.

The results of the DNA synthesis assay for the latter, non-tethered controls is shown in FIG. 1. The presence of EGF in the medium clearly causes an increase in the number of cells synthesizing DNA. The results of the DNA synthesis assay for the tethered EGF surface and the mock activated control surface that had only adsorbed EGF is shown in FIG. 2. The number of cells synthesizing DNA is clearly higher for the tethered EGF surface.

Modifications and variations of the compositions and methods of the present invention will be obvious to those skilled in the art from the foregoing detailed description. Such modifications and variations are intended to come within the scope of the appended claims.

We claim:

1. A method for growing eukaryotic cells comprising bringing into contact the cells with a composition comprising
    a biocompatible solid substrate,
    biocompatible polymeric tethers, and
    growth effector molecules,
    wherein one end of each tether is covalently linked to the substrate and one end is covalently linked to a growth effector molecule so that the growth effector molecule cannot be internalized by cells attached to the substrate;
    wherein the growth effector molecules are attached to the substrate in a concentration effective to enhance the rate of target cell growth over the rate of target cell growth with soluble growth effector molecules and growth effector molecules adsorbed to a substrate, without internalization of the molecules; and
    wherein the tether is covalently linked to the substrate and to the growth effector molecule by the same attachment agents, maintaining the cells in contact with the composition under conditions and for a time sufficient to cause the cells to grow.

2. The method of claim 1 wherein the attachment agent is selected from the group consisting of cyanogen bromide, succinimide, aldehyde, tosyl chloride, avidin-biotin, epoxide, maleimide, and carbodiimide.

3. The method of claim 2 wherein the composition is administered by injection, infusion, or implantation.

4. The method of claim 3 wherein the composition is administered by implantation of the composition and wherein the substrate is shaped to match a desired tissue shape.

5. The method of claim 4 wherein the substrate is biodegradable.

6. A method of testing a compound for an effect on tissue comprising bringing into contact the compound to be tested and a composition comprising
    a biocompatible solid substrate,
    biocompatible, polymeric tethers,
    growth effector molecules, and
    growing cells,
    wherein one end of each tether is covalently linked to the substrate and one end is covalently linked to a growth effector molecule so that the growth effector molecule cannot be internalized by cells attached to the substrate;
    wherein the growth effector molecules are attached to the substrate in a concentration effective to enhance the rate of target cell growth over the rate of target cell growth with soluble growth effector molecules and growth effector molecules adsorbed to a substrate, without internalization of the molecules;

wherein the tether is covalently linked to the substrate and to the growth effector molecule by the same attachment agents; and wherein the growing cells are bound to the growth effector molecules; incubating the compound and the composition under promoting cell growth; and observing the cells for any effect not observed in cells not brought into contact with the composition.

7. The method of claim 6 wherein the attachment agent is selected from, the group consisting of cyanogen bromide, succinimide, aldehyde, tosyl chloride, avidin-biotin, epoxide, maleimide, and carbodiimide.

* * * * *

UNITED STATES PATENT AND TRADEMARK OFFICE
CERTIFICATE OF CORRECTION

PATENT NO. : 7,008,634 B2
APPLICATION NO. : 08/398555
DATED : March 7, 2006
INVENTOR(S) : Linda G. Cima, Edward W. Merrill and Philip R. Kuhl It is certified that error appears in the above-identified patent and that said Letters Patent is hereby corrected as shown below:

In Claim 6 at column 15, line 8, insert --conditions-- between "under" and "promoting".

Signed and Sealed this

Sixth Day of February, 2007

JON W. DUDAS
*Director of the United States Patent and Trademark Office*